United States Patent
Parker et al.

(10) Patent No.: US 10,100,370 B2
(45) Date of Patent: Oct. 16, 2018

(54) COMPOSITIONS AND METHODS FOR DETECTING HUANGLONGBING

(71) Applicant: ENVIROLOGIX INC., Portland, ME (US)

(72) Inventors: Breck Parker, Portland, ME (US); Susan Tapley, Portland, ME (US); Paula Lampton, Portland, ME (US)

(73) Assignee: ENVIROLOGIX INC., Portland, ME (US)

(*) Notice: Subject to any disclaimer, the term of this patent is extended or adjusted under 35 U.S.C. 154(b) by 49 days.

(21) Appl. No.: 15/306,750

(22) PCT Filed: Apr. 28, 2015

(86) PCT No.: PCT/US2015/028006
§ 371 (c)(1),
(2) Date: Oct. 25, 2016

(87) PCT Pub. No.: WO2015/168134
PCT Pub. Date: Nov. 5, 2015

(65) Prior Publication Data
US 2017/0114394 A1    Apr. 27, 2017

Related U.S. Application Data

(60) Provisional application No. 61/986,587, filed on Apr. 30, 2014.

(51) Int. Cl.
| | | |
|---|---|---|
| *C07H 21/04* | (2006.01) | |
| *C12Q 1/68* | (2018.01) | |
| *C12Q 1/689* | (2018.01) | |

(52) U.S. Cl.
CPC ....... *C12Q 1/689* (2013.01); *C12Q 2600/156* (2013.01)

(58) Field of Classification Search
None
See application file for complete search history.

(56) References Cited

FOREIGN PATENT DOCUMENTS

| CN | 102605092 B | 6/2013 |
|---|---|---|
| WO | 2009/012246 A2 | 1/2009 |
| WO | 2013155056 A1 | 10/2013 |

OTHER PUBLICATIONS

Nageswara-Rao et al., "Candidate gene markers for Candidatus Liberibacter asiaticus for detecting citrus greening disease," J. Biosci. Mar. 15, 2013 (Mar. 15, 2013), vol. 38, pp. 229-237, entire document.

Rigano et al., "Rapid and sensitive detection of Candidatus Liberibacter asiaticus by loop mediated isothermal amplification combined with a lateral flow dipstick," BMC Microbiol. Apr. 6, 2014 (Apr. 6, 2014), vol. 14:86, pp. 1-9, entire document.

Kogenaru et al., "Repertoire of novel sequence signatures for the detection of Candidatus Liberibacter asiaticus by quantitative real-time PCR," BMC Microbiol. Feb. 17, 2014 (Feb. 17, 2014), vol. 14:39, pp. 1-11, entire document.

Ravidran et al., "Development of a loop-mediated isothermal amplification procedure as a sensitive and rapid method for detection of 'candidatus Liberibacter solanacearum' in potatoes and Psyllids," Phytopathology, Sep. 2012, vol. 102, pp. 889-907, entire document.

International Search Report and Written Opinion, for corresponding PCT/US2015/028006, dated Sep. 1, 2015 (14 pages).

Coy et al., "Nested-quantitative PCR approach with improved sensitivity for the detection of low titer levels of Candidatus Liberibacter asiaticus in the Asian citrus psyllid, Diaphorina citri Kuwayama", Journal of Microbiological Methods, vol. 102, Apr. 24, 2014, pp. 15-22.

Fujikawa et al., "Convenient Detection of the Citrus Greening (Huanglongbing) Bacterium 'Candidatus Liberibacter asiaticus' by Direct PCR from the Midrib Extract", PLOS One, vol. 8, No. 2, 20 Feb. 2013, pp. e57011.

Fujikawa et al., "Sensitive and robust detection of citrus greening (huanglongbing) bacterium "Candidatus Liberibacter asiaticus" by DNA amplification with new 16S rDNA-specific primers", Molecular and Cellular Probes, vol. 26, No. 5, Oct. 1, 2012, pp. 194-197.

Urasaki et al., "Rapid and sensitive detection of Candidatus Liberibacter asiaticus by cycleave isothermal and chimeric primer-initiated amplification of nucleic acids", Journal of General Plant Pathology, Springer-Verlag, TO, vol. 74, No. 2, Feb. 29, 2008, pp. 151-155.

Extended European Search Report for corresponding European Application No. 15785314.4, dated Nov. 23, 2017 (9 pages).

Office Action for corresponding Columbian application No. NC2016/004841, dated Jun. 13, 2018 (12 pages).

Ehses et al., "Optimization and Design of Oligonucleotide Setup for Strand Displacement Amplification", J Biochem Biophys Methods, Jun. 30, 2005; 63(3): 170-86, DOI: 10.1016/j.bbm.2005.04.005.

Razi et al., "Detection of Citrus Huanglongbing-Associated 'Candidatus Liberibacter asiaticus' in Citrus and Diaphorina Citri in Pakistan, (Continued)

*Primary Examiner* — Jeanine A Goldberg
(74) *Attorney, Agent, or Firm* — Melissa Hunter-Ensor; Greenberg Traurig, LLP

(57) ABSTRACT

The present invention features compositions and methods for detecting Huanglongbing (HLB) in citrus trees and insects. In one aspect, the invention provides a method of detecting a Huanglongbing (HLB) infection in a citrus grove involving obtaining an extract from a biological sample derived from a citrus grove, contacting the extract with forward and reverse primers that specifically bind a *Candidutus* nucleic acid molecule in the presence of a nicking enzyme, dNTPs, and a polymerase under conditions permissive for the isothermal amplification of the nucleic acid molecule; and detecting a *Candidutus* amplicon in the extract.

10 Claims, 6 Drawing Sheets
Specification includes a Sequence Listing.

(56) References Cited

OTHER PUBLICATIONS

Seasonal Variability, and Implications for Disease Management", Phytopathology, Mar. 2014; 104 (3):257-68, DOI: 10.1094/PHYTO-0813-0224-R.

Figure 1 Primers and Molecular Beacon Probe

- Forward Primer: Las.Laf.16S.12.77.fb     100nM

5'-GGACTCCATATGGAGTCCTCGCGAGCGGmCmAmGnAmC -3'

- Reverse Primer: Las.Laf.16S.12.100.rb     600nM

5'-TGACTCCATATGGAGTCATCTAGATTCCmUmAmCmGmC-3'

- Molecular Beacon Probe: HLB.83.F.CH CalRed     300nM

5'-CalRed$_{610nm}$-CACGCAmGCmAGmACmGGmGmUGmAGmUAmACmGTGCGTG-BHQ2-3'

Figure 2
- Prototype Citrus Greenin Assay
  - Detects HLB infection in psyllids and citrus petiole
  - 5 minute crude extraction from psyllids
  - 15 minute crude extraction from plant
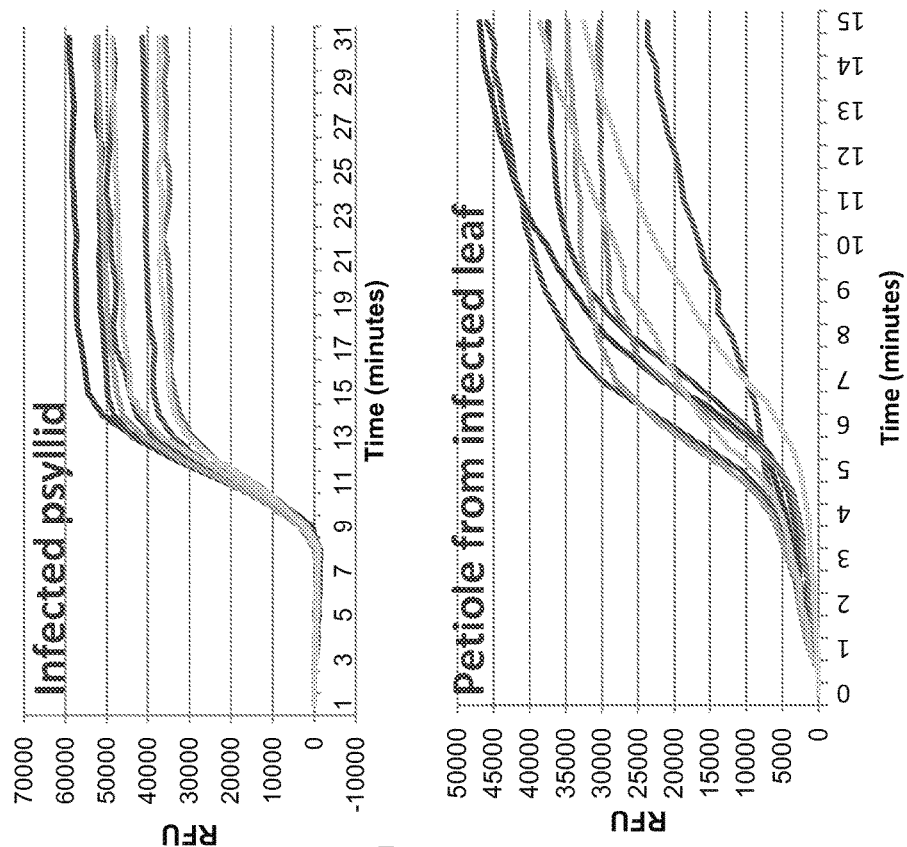
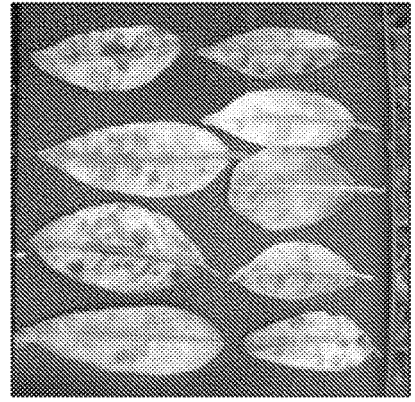

**HLB Assay Results
AmpliFire vs qPCR Instrument**

- Psyllid crude preparation used in two instruments
- Four replicates each of healthy and infected insects

Psyllid Product Insert

Figure 4

- Collect Psyllids from the field and place into 70% ethanol solution. Store refrigerated until time of testing.
- At the time of testing, remove DNAble kit components from refrigerated storage and allow all components to come to room temperature.
- Using the dropper bottle, carefully add 250 μl of MB3 extraction buffer. Add to the 0.25 mL line (in between the labeled 0.1 mL and 0.5 mL lines).
- At the time of testing, place each psyllid on a clean paper towel for 2 minutes to briefly dry off the ethanol. Clean forceps or a pipette tip with the end cut off work well for psyllid collection from ethanol. Place dried psyllid(s) in a sample extraction tube containing buffer. One to 10 psyllids may be pooled together into a single sample tube.
- Macerate psyllids in buffer with a blue pestle. Ensure that each psyllid has been macerated.
- Gently invert the tube 5 times to mix, then allow sample to settle for at least 3 minutes.
- 50 μl of each sample will be used directly in lyophilized master mix See file for complete procedure details

Adobe Acrobat Document

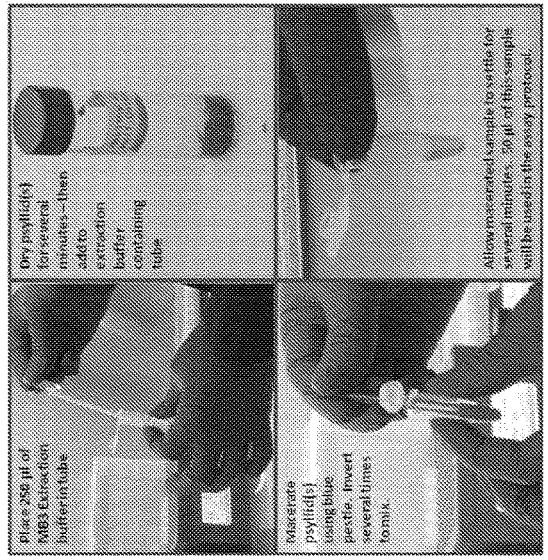

Petiole Protocol

Figure 5

- Collect sweet orange leaf and petiole sample (other species not yet evaluated). If sample will not be tested immediate, store refrigerated for 1-2 days, or frozen at -20°C for longer term storage.
- At the time of testing, remove DNAble kit components from refrigerated storage and allow all components to come to room temperature. Turn on a heat block set to 95°C and allow warming to temperature for at least 30 minutes.
- Add 400 µl of CE+0.5% sodium sulfite buffer to the tube.
- Using a clean, dry Harris punch, punch out four pieces of petiole starting from the bottom of the petiole. (Remove as little leaf tissue as possible)
- Add these 4 petiole punches to the buffer in tube.
- Heat sample at 95°C for 5 minutes.
- Remove from heat and add 400 µl of TE to sample.
- Vortex sample for 10 seconds to mix.
- 5 µl of each sample will be added to green reaction buffer strip.
- 50ul from reaction buffer strip will be added to lyophilized mastermix.
- For more detail see attached document (not updated for sample prep procedure)

Microsoft Office rd 97 - 2003 Docum

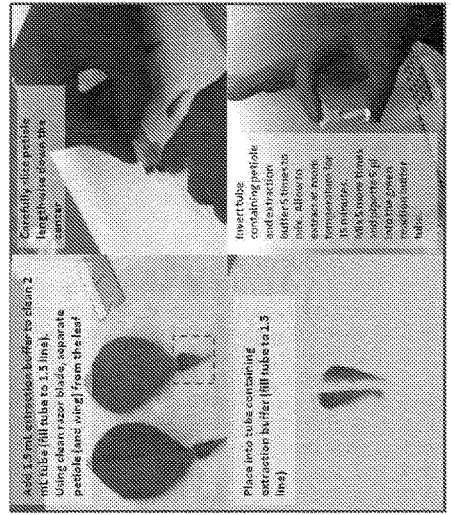

Figure 6

Lyophilization Setup

| | CHOCOLATE BEACON | Strips= | | |
|---|---|---|---|---|
| aliquot (x) | 4.0 | | | |
| | Stock Concentration | Lot # | per rxn (µl) | # rxns |
| LYO Buffer | | 110513KAC | 16.80 | 737.28 |
| | | | | 12386.30 |
| Forward Template (uM) T1 | | T2873 | 0.05 | 36.86 |
| Reverse Template (uM) T2 | | T2874 | 0.30 | 221.18 |
| Real-Time Probe (MB) | | T2872 | 0.15 | 110.59 |
| TE | | | 1.00 | 737.28 |
| dNTPs (mM) (1x) | 10 | A3035 | 1.50 | 1105.92 |
| Polymerase (units/ul) (1x) | 120 | 1/110612 | 0.16 | 117.96 |
| Nicking Enzyme (units/ul) (1x) | 160 | lot 27 gly free | 0.047 | 34.56 |
| | | Total Volume | 20.01 | 14750.67 |

COMPOSITIONS AND METHODS FOR DETECTING HUANGLONGBING

CROSS-REFERENCE TO RELATED APPLICATION

This application is the U.S. national phase application, pursuant to 35 U.S.C. § 371, of PCT International Application Ser. No. PCT/US2015/028006, filed Apr. 28, 2015, designating the United States and published in English, which claims priority to U.S. Provisional Patent Application Ser. No. 61/986,587, filed Apr. 30, 2014. The entire contents of each of the afore-mentioned applications are hereby incorporated by reference in their entirety.

BACKGROUND OF THE INVENTION

Huanglongbing (HLB), which is also known as citrus greening disease, is a fatal disease of citrus trees. Diseased trees are characterized by mottled leaves, poorly developed roots, and produce only a small number of hard, misshapen fruits that fail to ripen properly. Trees infected with HLB die within a few years. HLB is spread by an insect, the Asian citrus psyllid. Insects carrying HLB feed on healthy trees and transmit the bacteria responsible for causing HLB. Infected trees must be removed to protect other citrus trees. The disease is caused by a phloem limited bacteria that cannot be cultured.

HLB is a devastating diseases of citrus that threatens citrus production in the areas in which it occurs. HLB has been identified in Asia, Africa, the Indian subcontinent, and the Arabian Peninsula, Brazil, in the southern United States, and more recently in California. To date, control of the disease has been limited to the eradication of infected citrus plants, and control of the vector with systemic insecticides. Management of HLB has been seriously hampered by the lack of a definitive test that can identify diseased citrus trees. Introduction to identify HLB-infected trees and insects are urgently required.

SUMMARY OF THE INVENTION

As described below, the present invention features compositions and methods for detecting Huanglongbing (HLB) in citrus trees and insects.

In one aspect, the invention provides a method of detecting a Huanglongbing (HLB) infection in a citrus grove involving obtaining an extract from a biological sample derived from a citrus grove, contacting the extract with forward and reverse primers that specifically bind a *Candidutus* nucleic acid molecule in the presence of a nicking enzyme, deoxynucleotide triphosphates (dNTPs), and a polymerase under conditions permissive for the isothermal amplification of the nucleic acid molecule; and detecting a *Candidutus* amplicon in the extract, where the presence of the *Candidutus* amplicon detects an HLB infection in the citrus grove and failure to detect the amplicon indicates the absence of an HLB infection in the citrus grove.

In another aspect, the invention provides a method of detecting an HLB infection in a citrus sample involving contacting a citrus extract with forward and reverse primers that specifically bind a *Candidutus* nucleic acid molecule in the presence of a nicking enzyme, dNTPs, and a polymerase under conditions permissive for the isothermal amplification of the *Candidutus* nucleic acid molecule; and detecting the presence or absence of a *Candidutus* amplicon, where the presence of a *Candidutus* amplicon detects an HLB infection in the citrus sample and the absence of a *Candidutus* amplicon indicates the absence of an HLB infection in the citrus sample.

In another aspect, the invention provides a method of detecting an HLB infection in an insect involving contacting an insect extract with forward and reverse primers that specifically bind a *Candidutus* nucleic acid molecule in the presence of a nicking enzyme, dNTPs, and a polymerase under conditions permissive for the isothermal amplification of the HLB nucleic acid molecule; and detecting a *Candidutus* amplicon, where the presence of a *Candidutus* amplicon detects an HLB infection and the absence of a *Candidutus* amplicon indicates the absence of an HLB infection in the insect.

In another aspect, the invention provides a method for detecting HLB in a plant or insect, involving extracting a nucleic acid molecule from a plant or insect, contacting the extract with forward and reverse primers having the following sequences, respectively:

```
5' GGACTCCATATGGAGTCCTCGCGAGCGG-MeOC-MeOA-MeOG-
MeOA-MeOC 3'
and

5' TGACTCCATATGGAGTCATCTAGATTCC-MeOU-MeOA-MeOC-
MeOG-MeOC 3'
``` in the presence of a Nt.BstNBI(NEB) nicking enzyme, dNTPs, and a Bst DNA polymerase I for at least about ten minutes; and detecting the presence or absence of a *Liberibacter asiaticus* amplicon, where the presence of a *Liberibacter asiaticus* amplicon identifies an HLB infection in the plant or insect, and the absence of a *Liberibacter asiaticus* amplicon identifies the absence of an HLB infection in the plant or insect.

In another aspect, the invention provides a primer containing the nucleic acid sequence:

```
5' GGACTCCATATGGAGTCCTCGCGAGCGG-MeOC-MeOA-MeOG-
MeOA-MeOC 3'
or

5' TGACTCCATATGGAGTCATCTAGATTCC-MeOU-MeOA-MeOC-
MeOG-MeOC 3'.
```

In another aspect, the invention provides a pair of primers including a forward primer containing the nucleic acid sequence:

```
5' GGACTCCATATGGAGTCCTCGCGAGCGG-MeOC-MeOA-MeOG-
MeOA-MeOC 3'
``` and a reverse primer containing the nucleic acid sequence:

```
5' TGACTCCATATGGAGTCATCTAGATTCC-MeOU-MeOA-MeOC-
MeOG-MeOC 3'.
```

In another aspect, the invention provides a probe containing the nucleic acid sequence:

```
5' CACGCA-MeOG-C-MeOA-G-MeOA-C-MeOG-G-MeOG-MeOU-
G-MeOA-G-MeOU-A-MeOA-C-MeOG-TGCGTG 3'.
```

In another aspect, the invention provides a combination of primers and probes, including a forward primer containing the nucleic acid sequence:

5' GGACTCCATATGGAGTCCTCGCGAGCGG-MeOC-MeOA-MeOG-
MeOA-MeOC 3';

a reverse primer containing the nucleic acid sequence:

5' TGACTCCATATGGAGTCATCTAGATTCC-MeOU-MeOA-MeOC-
MeOG-MeOC 3';

and a detectable probe containing the nucleic acid sequence:

5' CACGCA-MeOG-C-MeOA-G-MeOA-C-MeOG-G-MeOG-MeOU-
G-MeOA-G-MeOU-A-MeOA-C-MeOG-TGCGTG 3'.

In another aspect, the invention provides a kit containing a forward primer containing the nucleic acid sequence:

5' GGACTCCATATGGAGTCCTCGCGAGCGG-MeOC-MeOA-MeOG-
MeOA-MeOC 3';

a reverse primer containing the nucleic acid sequence:

5' TGACTCCATATGGAGTCATCTAGATTCC-MeOU-MeOA-MeOC-
MeOG-MeOC 3';

and a detectable probe containing the nucleic acid sequence:

5' CACGCA-MeOG-C-MeOA-G-MeOA-C-MeOG-G-MeOG-MeOU-G-
MeOA-G-MeOU-A-MeOA-C-MeOG-TGCGTG 3'. In certain embodiments, the kit includes one or more of a nicking enzyme, deoxynucleotide triphosphates (dNTPs) (e.g., dATP, dCTP, dGTP, dTTP), and a polymerase.

In various embodiments of any aspect delineated herein, the citrus grove contains one or more of sweet orange, sour orange, mandarin, kumquat, tangerine, tangelo, lemon, lime, grapefruit, pumelo, Mexican lime, or combava. In various embodiments of any aspect delineated herein, the biological sample is or contains plant, insect, or plant and insect material. In various embodiments, the sample is one or more of leaf midrib, petiole, leaf blade, bark, or fruit tissue. In various embodiments, the fruit tissue is or contains pulp (e.g., orange pulp), juice (e.g., orange juice), locular membrane, septa, endocarp, peduncle, central axis, and pericarp. In various embodiments of any aspect delineated herein, the citrus sample is or contains one or more of sweet orange, sour orange, mandarin, kumquat, tangerine, tangelo, lemon, lime, grapefruit, pumelo, Mexican lime, or combava.

In various embodiments of any aspect delineated herein, the insect is a psyllid, including *Diaphorina citri*. In various embodiments, the insect is an insect egg, nymph, or adult.

In various embodiments of any aspect delineated herein, the *Candidutus* bacteria is one or more of *Candidutus liberibacter asiaticus, Candidutus liberibacter africanus,* or *Candidutus liberibacter americanus*.

In various embodiments of any aspect delineated herein, the forward and reverse primers contain the following sequences, respectively:

5' GGACTCCATATGGAGTCCTCGCGAGCGG-MeOC-MeOA-MeOG-
MeOA-MeOC 3'
and

5' TGACTCCATATGGAGTCATCTAGATTCC-MeOU-MeOA-MeOC-
MeOG-MeOC 3'

In various embodiments of any aspect delineated herein, amplification is detected using a probe containing the following sequence:

5' CACGCA-MeOG-C-MeOA-G-MeOA-C-MeOG-G-MeOG-MeOU-
G-MeOA-G-MeOU-A-MeOA-C-MeOG-TGCGTG 3'.

In various embodiments of any aspect delineated herein, the nicking enzyme is one or more of N.Bst9I, N.BstSEI, Nb.BbvCI(NEB), Nb.Bpu10I(Fermantas), Nb.BsmI(NEB), Nb.BsrDI(NEB), Nb.BtsI(NEB), Nt.AlwI(NEB), Nt.BbvCI (NEB), Nt.Bpu10I(Fermentas), Nt.BsmAI, Nt.BspD6I, Nt.BspQI(NEB), Nt.BstNBI(NEB), and Nt.CviPII(NEB).

In various embodiments of any aspect delineated herein, the polymerase is Bst DNA polymerase I or Gst DNA polymerase I.

In various embodiments of any aspect delineated herein, a method of the invention is used periodically to monitor a citrus grove or other area for the presence of HLB. In various embodiments, the monitoring is conducted every 3, 6, 9, or 12 months.

The invention provides for the identification of HLB infected trees and insects. Compositions and articles defined by the invention were isolated or otherwise manufactured in connection with the examples provided below. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "amplicon" is meant a polynucleotide generated during the amplification of a target polynucleotide of interest.

By "base substitution" is meant a substituent of a nucleobase polymer that does not cause significant disruption of the hybridization between complementary nucleotide strands.

By "complementary" or "complementarity" is meant that a nucleic acid can form hydrogen bond(s) with another nucleic acid sequence by either traditional Watson-Crick or Hoogsteen base pairing. Complementary base pairing includes not only G-C and A-T base pairing, but also includes base pairing involving universal bases, such as inosine. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). To determine that a percent complementarity is of at least a certain percentage, the percentage of contiguous residues in a nucleic acid molecule that can form hydrogen bonds (e.g., Watson-Crick base pairing) with a second nucleic acid sequence is calculated and rounded to the nearest whole number (e.g., 12, 13, 14, 15, 16, or 17 nucleotides out of a total of 23 nucleotides in the first oligonucleotide being based paired to a second nucleic acid sequence having 23 nucleotides represents 52%, 57%, 61%, 65%, 70%, and 74%, respectively; and has at least 50%, 50%, 60%, 60%, 70%, and 70% complementarity, respectively). As used herein, "substantially complementary" refers to complementarity between the strands such that they are capable of hybridizing under biological conditions. Substantially complementary sequences have 60%, 70%, 80%, 90%, 95%, or even 100% complementarity. Additionally, techniques to determine if two strands are capable of hybridizing under biological conditions by examining their nucleotide sequences are well known in the art.

As used herein, "duplex" refers to a double helical structure formed by the interaction of two single stranded nucleic acids. A duplex is typically formed by the pairwise hydrogen bonding of bases, i.e., "base pairing", between two single stranded nucleic acids which are oriented antiparallel with respect to each other. Base pairing in duplexes generally occurs by Watson-Crick base pairing, e.g., guanine (G) forms a base pair with cytosine (C) in DNA and RNA, adenine (A) forms a base pair with thymine (T) in DNA, and adenine (A) forms a base pair with uracil (U) in RNA. Conditions under which base pairs can form include physiological or biologically relevant conditions (e.g., intracellular: pH 7.2, 140 mM potassium ion; extracellular pH 7.4, 145 mM sodium ion). Furthermore, duplexes are stabilized by stacking interactions between adjacent nucleotides. As used herein, a duplex may be established or maintained by base pairing or by stacking interactions. A duplex is formed by two complementary nucleic acid strands, which may be substantially complementary or fully complementary. Single-stranded nucleic acids that base pair over a number of bases are said to "hybridize."

"Detect" refers to identifying the presence, absence or amount of the analyte to be detected.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides.

By "hybridize" is meant to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507). Hybridization occurs by hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "monitoring a reaction" is meant detecting the progress of a reaction. In one embodiment, monitoring reaction progression involves detecting polymerase extension and/or detecting the completion of an amplification reaction.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, 2′ modified nucleotides (e.g., 2′-O-methyl ribonucleotides, 2′-F nucleotides).

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2′ modifications, e.g., 2′-O-methyl, 2′-methoxyethoxy, 2′-fluoro, 2′-hydroxyl (RNA), 2′-allyl, 2′-O-[2-(methylamino)-2-oxoethyl], 4′-thio, 4′-CH$_2$—O-2′- bridge, 4'-(CH$_2$)$_2$—O-2'-bridge, and 2'-O—(N-methylcarbamate) or those comprising base analogs.

By "nicking agent" is meant a chemical entity capable of recognizing and binding to a specific structure in double stranded nucleic acid molecules and breaking a phosphodiester bond between adjoining nucleotides on a single strand upon binding to its recognized specific structure, thereby creating a free 3'-hydroxyl group on the terminal nucleotide preceding the nick site. In preferred embodiments, the 3' end can be extended by an exonuclease deficient polymerase. Exemplary nicking agents include nicking enzymes, RNAzymes, DNAzymes, and transition metal chelators.

By "polymerase-arresting molecule" is meant a moiety associated with a polynucleotide that prevents or significantly reduces the progression of a polymerase on the polynucleotide template. Preferably, the moiety is incorporated into the polynucleotide. In one preferred embodiment, the moiety prevents the polymerase from progressing on the template.

By "polymerase extension" is meant the forward progression of a polymerase that matches incoming monomers to their binding partners on a template polynucleotide.

By "semi-quantitative" is meant providing an estimate of relative quantity based on an internal control.

By "specific product" is meant a polynucleotide product resulting from the hybridization of primer oligonucleotides to a complementary target sequence and subsequent polymerase mediated extension of the target sequence.

By "substantially isothermal condition" is meant at a single temperature or within a narrow range of temperatures that does not vary significantly. In one embodiment, a reaction carried out under substantially isothermal conditions is carried out at a temperature that varies by only about 1-5° C. (e.g., varying by 1, 2, 3, 4, or 5 degrees). In another embodiment, the reaction is carried out at a single temperature within the operating parameters of the instrument utilized.

By "target nucleic acid molecule" is meant a polynucleotide to be analyzed. Such polynucleotide may be a sense or antisense strand of the target sequence. The term "target nucleic acid molecule" also refers to amplicons of the original target sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 provides the sequences of primer oligonucleotides and a molecular beacon probe for use in amplifying and detecting an HLB nucleic acid molecule.

FIG. 2 provides an exemplary HLB Assay, and provides results for the detection of HLB amplicons extracted from psyllids or leaf petioles.

FIG. 4 shows an assay protocol for extracting HLB polynucleotides from psyllids.

FIG. 5 shows an assay protocol for extracting HLB polynucleotides from leaf petioles.

FIG. 6 shows the amount of various reagents used in an HLB protocol.

DETAILED DESCRIPTION OF THE INVENTION

Figure 3:
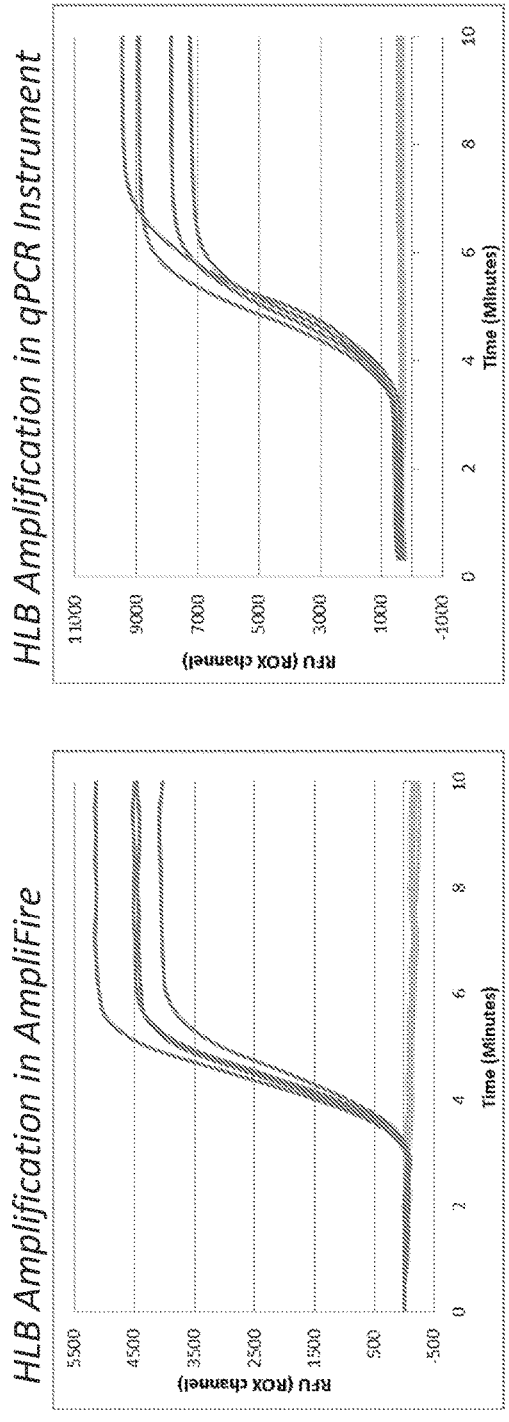
FIG. 3 shows HLB assay results obtained in AmpliFire or a qPCR instrument.

The invention features compositions and methods that are useful for the identification of HLB in insects and infected plants by amplifying the 16S RNA gene.

The invention is based, at least in part, on the discovery that a Huanglongbing infection can be detected by assaying plant or insect samples using an isothermal nicking amplification reaction.

Huanglongbing Detection

Huanglongbing (HLB) is a fatal bacterial disease affecting *Citrus*. Because the bacteria associated with HLB cannot be cultured, HLB detection has relied on the identification of citrus trees having symptoms of HLB. This has proved problematic given that symptoms of HLB infection can take two years or more to manifest. In the meantime, the fatal disease can spread.

HLB is associated with *Candidutus* bacteria, including but not limited to, *Candidutus* liberibacter asiaticus, *Candidutus* liberibacter africanus, *Candidutus* liberibacter americanus. The present invention provides methods of *Candidutus* liberibacter asiaticus and *Candidutus* liberibacter africanus that involve amplifying the 16S RNA region from the bacteria.

*Citrus* comprises flowering trees and shrubs, including but not limited to *Citrus aurantiifolia* (Key Lime, Omani Lime), *Citrus crenatifolia, Citrus maxima* (Pomelo (pummelo, shaddock), *Citrus medica* (Citron), *Citrus reticulata* (Mandarin orange), *Citrus trifoliata* (Trifoliate orange), *Citrus australasica* (Australian Finger Lime), *Citrus australis* (Australian Round lime), *Citrus glauca* (Australian Desert Lime), *Citrus garrawayae* (Mount White Lime), *Citrus gracilis* (Kakadu Lime or Humpty Doo Lime), *Citrus inodora* (Russel River Lime) *Citrus warburgiana* (New Guinea Wild Lime), *Citrus wintersii* (Brown River Finger Lime), *Citrus japonica* (Kumquats), *Citrus halimii* (Papedas), *Citrus indica* (Indian wild orange), *Citrus macroptera*, and *Citrus latipes*. According to the methods of the invention, HLB infection is detected in a plant extract (e.g., leaf midribs, petiole, leaf blade, bark, and fruit tissue, such as locular membrane, septa, endocarp, peduncle, central axis, and pericarp).

HLB is transmitted by psyllids (Psyllidae), which are aphid-like insects that tend to be fairly host specific. In particular, HLB is transmitted by the Asian citrus psyllid *Diaphorina citri*, which acts as an HLB disease vector. According to the methods of the invention, an HLB infection is detected in a psyllid extract (e.g., extract of adult, nymph, or a combination thereof).

Psyllid infested groves or plants must be destroyed to prevent the infestation from spreading. Accordingly, detection of a psyllid infestation may be carried out in a variety of locations where citrus plants are grown, housed, transported, or processed. The invention provides compositions for identifying an HLB-infected psyllid or plant in a citrus grove, nursery, green house, warehouse, truck, or market or in trees grown by home owners.

To prevent spread of HLB, it may be important to monitor citrus fruit that may harbor an HLB-infected psyllid or HLB infection. Produce infected with HLB and/or carrying HLB-infected psyllids can be identified at a variety of points along the supply chain, including but not limited to, in groves, warehouses, trucks, and markets.

HLB is also detectable in the juice, pulp, and other materials isolated from oranges during food processing.

Nucleic Amplification Methods

The present invention provides nucleic acid amplification technology for the detection of HLB in plant, insects, or a combination of such materials collected from citrus trees by detecting the presence or absence of a *Candidutus* polynucleotide in a plant or insect extract. In particular embodiments, an *Candidutus* nucleic acid molecule is amplified in an isothermal nicking amplification reaction that employs oligonucleotide primers that are complementary to an *Candidutus* target sequence, resulting in a logarithmic increase in the target sequence. The nicking amplification reaction progresses isothermally, in contrast to the polymerase chain reaction ("PCR"). In PCR, the temperature is increased to allow the two strands of DNA to separate. In a nicking amplification reaction, primer molecules anneal to the complementary sequence from the added exogenous DNA. The polymerase begins complementary strand synthesis of the target nucleotide sequence (the added exogenous DNA) from the 3' end of the primer along with displacement of the existing complementary DNA strand. In some embodiments, the target nucleic acid sequence is nicked at specific nicking sites present in the test sample. The strand displacement replication process obviates the need for increased temperature. The second oligonucleotide primer anneals to the newly synthesized complementary strand and extends making a duplex of DNA which includes the nicking enzyme recognition sequence. This strand is then liable to be nicked with subsequent strand displacement extension by the polymerase, which leads to the production of a duplex of DNA which has nick sites on either side of the original target DNA. Once this is synthesized, the molecule continues to be amplified exponentially through replication of the displaced strands with new primer molecules, generating amplicons of the target nucleic acid molecule. In addition, amplification also proceeds linearly from each product molecule through the repeated action of the nick translation synthesis at the primer introduced nick sites. The result is a very rapid increase in target signal amplification; much more rapid than PCR thermocycling, with amplification results in less than ten minutes. This provides for the identification of an HLB infection within the sample shortly after sample collection. In particular, the invention provides for the on-site testing of samples within a citrus grove, nursery, green house, transportation facility, truck, warehouse, market, or other site where a HLB-infected psyllid infestation, HLB infection, or the presence of HLB infected materials is suspected.

Nicking Amplification Assays

The invention provides for the detection of target *Candidutus* nucleic acid molecules amplified in an isothermal nicking amplification assay. Such assays are known in the art and described herein. See, for example, US Patent Application Publication 2015/0104788, which is incorporated herein in its entirety. Polymerases useful in the methods described herein are capable of catalyzing the incorporation of nucleotides to extend a 3' hydroxyl terminus of an oligonucleotide (e.g., a primer) bound to a target nucleic acid molecule. Such polymerases include those that are thermophilic and/or those capable of strand displacement. In one embodiment, a polymerase lacks or has reduced 5'-3' exonuclease activity and/or strand displacement activity. DNA polymerases useful in methods involving primers having 2'-modified nucleotides at the 3' end include derivatives and variants of the DNA polymerase I isolated from *Bacillus stearothermophilus*, also taxonomically re-classified as *Geobacillus stearothermophilus*, and closely related thermophilic bacteria, which lack a 5'-3' exonuclease activity and have strand-displacement activity. Exemplary polymerases include, but are not limited to the fragments of Bst DNA polymerase I and Gst DNA polymerase I.

A nicking enzyme binds double-stranded DNA and cleaves one strand of a double-stranded duplex. In the methods of the invention, the nicking enzyme cleaves the top stand (the strand comprising the 5'-3' sequence of the nicking agent recognition site). In a particular embodiment of the invention disclosed herein, the nicking enzyme cleaves the top strand only and 3' downstream of the recognition site. In exemplary embodiments, the reaction comprises the use of a nicking enzyme that cleaves or nicks downstream of the binding site such that the product sequence does not contain the nicking site. Using an enzyme that cleaves downstream of the binding site allows the polymerase to more easily extend without having to displace the nicking enzyme. Ideally, the nicking enzyme is functional under the same reaction conditions as the polymerase. Exemplary nicking enzymes include, but are not limited to, N.Bst9I, N.BstSEI, Nb.BbvCI(NEB), Nb.Bpu10I(Fermantas), Nb.BsmI(NEB), Nb.BsrDI(NEB), Nb.BtsI(NEB), Nt.AlwI(NEB), Nt.BbvCI(NEB), Nt.Bpu10I(Fermentas), Nt.BsmAI, Nt.BspD6I, Nt.BspQI(NEB), Nt.BstNBI(NEB), and Nt.CviPII(NEB).

A nicking amplification reaction typically comprises nucleotides, such as, for example, dideoxyribonucleoside triphosphates (dNTPs). The reaction may also be carried out in the presence of dNTPs that comprise a detectable moiety including but not limited to a radiolabel (e.g., $^{32}$P, $^{33}$P, $^{125}$I, $^{35}$S) an enzyme (e.g., alkaline phosphatase), a fluorescent label (e.g., fluorescein isothiocyanate (FITC)), biotin, avidin, digoxigenin, antigens, haptens, or fluorochromes. The reaction further comprises certain salts and buffers that provide for the activity of the nicking enzyme and polymerase.

Advantageously, the nicking amplification reaction is carried out under substantially isothermal conditions where the temperature of the reaction is more or less constant during the course of the amplification reaction. Because the temperature does not need to be cycled between an upper temperature and a lower temperature, the nicking amplification reaction can be carried out under conditions where it would be difficult to carry out conventional PCR. Typically, the reaction is carried out at about between 35° C. and 90° C. (e.g., about 35°, 37°, 42°, 55°, 56°, 60°, 65°, 70°, 75°, 80°, or 85° C.). Advantageously, it is not essential that the temperature be maintained with a great degree of precision. Some variability in temperature is acceptable.

This invention provides methods of monitoring a nicking amplification reaction in real time, utilizing the amplification strategy as described above and in U.S. Patent Application Publication 2015/0104788. In one embodiment, quantitative nucleic acid amplification utilizes target nucleic acids amplification alongside a control amplification of known quantity. The amount of target nucleic acid can be calculated as an absolute quantification or a relative quantification (semi-quantitative) based on the source of the control (exogenous or endogenous control).

Quantification of the unknown nucleotide sequence can be achieved either through comparison of logarithmic threshold amplification of the unknown to a series of known target sequences in either a separate set of reactions or in the same reaction; or as an internal endogenous or exogenous co-amplification product which produces a threshold value, indicative of either a positive result (if the unknown exceeds the threshold) or negative result (if the unknown does not exceed the threshold).

Primers

The invention provides primers that specifically target a *Candidutus* nucleic acid molecule. Preferably, the target recognition sequence within the primer comprises at least about 25, 26, 27, 28, 29, 30, 35 nucleotides. Such primers are useful for amplifying a *Candidutus* target nucleic acid molecule in a nicking amplification assay. Preferably, the 3' end of the primer comprises one or more (e.g., 1, 2, 3, 4, 5, 6, 7) 2' modified nucleotides (e.g., 2'-O-methyl, 2'-methoxyethoxy, 2'-fluoro, 2'-alkyl, 2'-allyl, 2'-O-[2-(methylamino)-2-oxoethyl], 2'-hydroxyl (RNA), 4'-thio, 4'-CH$_2$—O-2'-bridge, 4'-(CH$_2$)$_2$—O-2'-bridge, and 2'-O—(N-methylcarbamate)). Without being bound to theory, it is hypothesized that incorporating one or more 2' modified nucleotides reduces or eliminates the background signal in isothermal amplification. The 2' modified nucleotide preferably has a base that base pairs with the target sequence. In particular embodiments, two or more 2' modified nucleotides (e.g., 2, 3, 4, 5 or more 2' modified nucleotides) in the target specific recognition region are contiguous (e.g., a block of modified nucleotides). In some embodiments, the block of 2' modified nucleotides is positioned at the 3' end of the target specific recognition region.

Detectable Oligonucleotide Probes

The present invention provides for the quantitative detection of target *Candidutus* nucleic acid molecules or amplicons thereof in a nicking amplification reaction using non-amplifiable detectable polynucleotide probes comprising at least one polymerase-arresting molecule (e.g., nucleotide modification or other moiety that renders the oligonucleotide capable of binding a target nucleic acid molecule, but incapable of supporting template extension utilizing the detectable oligonucleotide probe as a target). Without wishing to be bound by theory, the presence of one or more moieties which does not allow polymerase progression likely causes polymerase arrest in non-nucleic acid backbone additions to the oligonucleotide or through stalling of a replicative polymerase (i.e. C3-spacer, damaged DNA bases, other spacer moiety, O-2-Me bases). These constructs thus prevent or reduce illegitimate amplification of the probe during the course of a nicking amplification reaction. This distinguishes them from conventional detection probes, which must be added at the end of the nicking amplification reaction to prevent their amplification.

Conventional detection probes have proven impractical for quantitating a nicking amplification reaction in real time. If conventional detection probes are incorporated into the nicking amplification reaction, these conventional detection probes are amplified concurrently with the target. The amplification of these detection molecules masks the detection of legitimate target amplicons due to the number of starting molecules of the detection probe at the start of the reaction.

The invention provides non-amplifiable detectable polynucleotide probe that comprise least one polymerase-arresting molecule. A polymerase-arresting molecule of the invention includes, but is not limited to, a nucleotide modification or other moiety that blocks primer extension by replicative DNA polymerases, thereby preventing the amplification of detection molecules; but can allow proper hybridization or nucleotide spacing to the target molecule or amplified copies of the target molecule. In one embodiment, a detectable oligonucleotide probe of the invention comprises a 3 carbon spacer (C3-spacer) that prevents or reduces the illegitimate amplification of a detection molecule.

In one embodiment, a detectable oligonucleotide probe comprises one or more modified nucleotide bases having enhanced binding affinity to a complementary nucleotide. Examples of modified bases include, but are not limited to 2' Fluoro amidites, and 2'OMe RNA amidites (also functioning as a polymerase arresting molecule). Detectable oligonucleotide probes of the invention can be synthesized with different colored fluorophores and may be designed to hybridize with virtually any target sequence. In view of their remarkable specificity, a non-amplifiable detectable polynucleotide probe of the invention is used to detect a single target nucleic acid molecule in a sample, or is used in combination with detectable oligonucleotide probes each of which binds a different target nucleic acid molecule. Accordingly, the non-amplifiable detectable polynucleotide probes of the invention may be used to detect one or more target nucleic acid molecules in the same reaction, allowing these targets to be quantitated simultaneously. The present invention encompasses the use of such fluorophores in conjunction with the detectable oligonucleotide probes described herein.

Use of Non-Amplifiable Detectable Polynucleotide Probes

Non-amplifiable detectable polynucleotide probe are useful in methods for quantitating a target nucleic acid molecule in a nicking amplification reaction. The method involves contacting a target nucleic acid molecule (e.g., a *Candidutus* nucleic acid molecule) under substantially isothermal conditions with a polymerase, two primers, each of which specifically binds to a complementary sequence on the target nucleotide molecule, a nicking enzyme, and a detectable oligonucleotide probe in the presence of a suitable buffer and dNTPs, generating amplicons comprising at least a portion of said target nucleic acid molecule; and determining the level of target nucleic acid molecule present in the reaction by quantitating the oligonucleotide probe that hybridizes to the target nucleic acid molecule. If desired, this may be done in real time during the reaction based on fluorescent intensity from the probe molecules in the reaction.

In general, non-amplifiable detectable polynucleotide probes of the invention are included in a nicking amplification reaction that comprises (1) a target nucleic acid molecule; (2) two primers comprising some number of oligonucleotides that are complementary to the target nucleic acid molecule and a site that can be cleaved by a nicking enzyme; (3) dNTPs; (4) a strand displacing polymerase; and (5) a nicking enzyme. Accordingly, the invention provides a method of using these components to quantitate a target HLB nucleic acid molecule.

Kits

The invention also provides kits for the detection of a target *Candidutus* nucleic acid molecule. Such kits are useful for the detection or quantitation of a target *Candidutus* nucleic acid in a biological sample (e.g., plant, insect, mixed plant/insect sample). Kits of the present invention may comprise, for example, one or more polymerases, forward and reverse primers, and one or more nicking enzymes, and a probe as described herein. Where one target is to be amplified, one or two nicking enzymes may be included in the kit.

The kits of the present invention may also comprise one or more of the components in any number of separate containers, packets, tubes (e.g., <0.2 ml, 0.2 ml, 0.6 ml, 1.5 ml, 5.0 ml, >5.0 ml), vials, microtiter plates (e.g., <96-well, 96-well, 384-well, 1536-well, >1536-well), ArrayTape, and the like, or the components may be combined in various combinations in such containers. In various embodiments, the kit further comprises a pair of primers capable of binding to and amplifying a reference sequence that can be used as a positive control. In yet other embodiments, the kit comprises a sterile container which contains the primers; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The components of the kit may, for example, be present in one or more containers, for example, all of the components may be in one container, or, for example, the enzymes may be in a separate container from the primers. The components may, for example, be dried (e.g., powder) or in a stable buffer (e.g., chemically stabilized, thermally stabilized). Dry components may, for example, be prepared by lyophilization, vacuum and centrifugal assisted drying and/or ambient drying. In various embodiments, the polymerase and nicking enzymes are in lyophilized form in a single container, and the primers are either lyophilized, freeze dried, or in buffer, in a different container. In some embodiments, the polymerase, nicking enzymes, and the primers are, in lyophilized form, in a single container. In other embodiments, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Kits may further comprise reagents used for detection methods, such as, for example, hybridization probes or DNA binding dyes. Detection components may be incorporated into a lateral flow device. The lateral flow device may be used at a point of care.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Test Kit for Qualitative Detection of DNA from *Liberibacter Asiaticus*

Rapid, point of need detection of huanglongbing (HLB) is required to effect interventions to prevent its spread. Huanglongbing, also known as citrus greening disease, causes yellowing of plant tissues, production of aberrantly formed fruit, and ultimately death of the plant. Asian citrus psyllids are a carrier of the pathogen. A test kit was generated for qualitative detection of DNA from *Liberibacter asiaticus*. The complete genome of *Candidatus Liberibacter asiaticus* str. psy62, is known and was deposited at NCBI ACCESSION No. CP001677.

The detection assay is based on an isothermal nucleic acid amplification method. An assay target sequence in the *Liberibacter asiaticus* was selected based on the absence of single nucleotide polymorphisms (SNP's) in a 30 to 60 bp sequence window. The following primers were used for amplification of the target nucleic acid molecule (FIG. 1).

```
Forward Primer T1: Las.Laf.16S.12.77.fb 100 nM
(MeO = 2' methoxy nucleotide)
5'-GGACTCCATATGGAGTCCTCGCGAGCGG-MeOC-MeOA-MeOG-
MeOA-MeOC-3'

Reverse Primer T2: Las.Laf.16S.12.100.rb 600 nM
(MeO = 2' methoxy nucleotide)
5'-TGACTCCATATGGAGTCATCTAGATTCC-MeOU-MeOA-MeOC-
MeOG-MeOC-3'
```

The following probe was used for detection of the target nucleic acid molecule:

Probe MB:HLB.83.F.CH CalRed 300 nM (MeO=2' methoxy nucleotide)

5'-Cal red610 CACGCA-MeOG-C-MeOA-G-MeOA-C-MeOG-G-MeOG-MeOU-G-MeOA-G-MeOU-A-MeOA-C-MeOG-TGCGTG-BHQ-3'

The above primers and probes were tested in isothermal nucleic acid amplification reactions as described in FIG. 6. Test samples were prepared from psyllids infected with *Liberibacter asiaticus* or petioles of leaves infected with *Liberibacter asiaticus*. Nucleic acid amplification of the target nucleic acid was detected with the primer-probe combination using samples from infected psyllids (FIG. 2). The amplification and detection reactions displayed a high signal to noise ratio, early onset of exponential amplification, steep amplification slope, rapid time to detection, and low signal variance among replicated assay reactions. For samples from petioles of leaves infected, the assay showed detection of the target nucleic acid molecule with high signal to noise ratio and early onset of exponential amplification (FIG. 2).

To test instrument variability in signal detection, two different instruments were used to quantify the signals. Both instruments showed assay results with a high signal to noise ratio, early onset of exponential amplification, steep amplification slope, rapid time to detection, and low signal variance among replicated assays (FIG. 3). No target control samples showed no signal when the assays were performed in either of the test instruments (FIGS. 3A and 3B). These results indicate that the foregoing reaction and reagents can be used for rapid, detection of *Liberibacter asiaticus*.

The invention was made using the following materials and methods. The detection assay is also performed using the materials and methods.

Psyllid Sample Collection and Preparation

Psyllids from the field were collected and placed into an ethanol solution (70%). The psyllid samples were refrigerated until time of testing. Test kit components were also stored at 4° C. until time of testing. At time of testing, assay components were allowed to come to room temperature. Individual psyllids were removed from the ethanol solution and allowed to dry briefly before being placed in a sample extraction tube containing extraction buffer (MB3, 250 µl) (FIG. 4). One to 10 psyllids were pooled together into a single sample tube. Psyllids were macerated in buffer with a pestle. The test tube was gently inverted (e.g., 5 times) to mix, then the sample was allowed to settle for at least 3 minutes.

Petiole Sample Collection and Preparation

Sweet orange leaf and petiole sample were collected and processed as described in FIG. 5 The psyllid samples were refrigerated 1-2 days until time of testing. In other experiments, psyllid samples were frozen at −20° C. for longer term storage. Test kit components were also stored at 4° C. until time of testing. At time of testing, assay components were allowed to come to room temperature. Using a clean, dry Harris punch, petiole samples were punched out starting from the bottom of the petiole, (remove as little leaf tissue as possible). The petiole punches (e.g., n=4) were added to a test tube containing extraction buffer (CE+0.5% sodium sulfite buffer, 400 µl). The sample was heated at 95° C. for 5 minutes. At the end of the incubation at 95° C., TE (400 µl) was added to the sample and mixed by vortexing (e.g., for 10 sec.).

Nucleic Acid Detection Assay

In one embodiment, the assay includes test tubes containing lyophilized reagents (primers, probes, etc.; see FIG. 6) in the form of a pellet and a strip for closing the test tubes. Sample (5-50 µl) is directly added to lyophilized master mix. The reaction is incubated at 56° C. for 10-15 minutes and a fluorescence signal recorded. The presence of fluorescence relative to a negative control indicates the presence of HLB in the sample.

The master mix includes 16.8 µl of LYO buffer, 0.06 µl of Forward primer, 0.3 µl of reverse primer, 0.15 µl of real-time probe (MB), 1.0 µl of TE (Tris EDTA, 1.5 µl of dNTPs (mM), 0.16 µl of Bst DNA polymerase I, 0.47 µl of nicking enzyme Nt.BstNBI (NEB).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A polynucleotide selected from the group consisting of a forward primer comprising (SEQ ID NO: 1)
5' GGACTCCATATGGAGTCCTCGCGAGCGG-MeOC-MeOA-MeOG-MeOA-MeOC 3', a reverse primer comprising the nucleic acid sequence (SEQ ID NO: 2)
5' TGACTCCATATGGAGTCATCTAGATTCC-MeOU-MeOA-MeOC-MeOG-MeOC 3';

and
a probe comprising (SEQ ID NO: 3)
5' CACGCA-MeOG-C-MeOA-G-MeOA-C-MeOG-G-MeOG-MeOU-G-MeOA-G-MeOU-A-MeOA-C-MeOG-TGCGTG 3'.

2. A kit comprising one or more polynucleotides of claim 1.

3. A method of detecting a Huanglongbing (HLB) infection in a biological sample, the method comprising obtaining an extract from a biological sample, contacting the extract with forward and reverse primers that specifically bind a *Candidutus* nucleic acid molecule in the presence of a nicking enzyme, dNTPs, and a polymerase under conditions permissive for the isothermal amplification of the nucleic acid molecule;

wherein the forward and reverse primers comprise the following sequences, respectively:

```
                                              (SEQ ID NO: 1)
5' GGACTCCATATGGAGTCCTCGCGAGCGG-MeOC-MeOA-MeOG-
MeOA-MeOC 3'
and (SEQ ID NO: 2)
5' TGACTCCATATGGAGTCATCTAGATTCC-MeOU-MeOA-MeOC-
MeOG-MeOC 3'
```
and deleting a *Candidutus* amplicon in the extract, wherein the presence of the *Candidutus* amplicon detects an HLB infection in the sample and failure to detect the amplicon indicated the absence of an HLB infection in the sample.

4. The method of claim 3, wherein the biological sample comprises plant, insect, or plant and insect material.

5. The method of claim 4, wherein the insect is a psyllid.

6. The method of claim 5, wherein the psyllid is *Diaphorina citri*.

7. The method of claim 3, wherein the method detects an HLB infection in a citrus grove selected from the group consisting of sweet orange, sour orange, mandarin, kumquat, tangerine, tangelo, lemon, lime, grapefruit, pumelo, Mexican lime, and combava.

8. The method of claim 3, wherein the biological sample is selected from the group consisting of sweet orange, sour orange, mandarin, kumquat, tangerine, tangelo, lemon, lime, grapefruit, pumelo, Mexican lime, and combava.

9. The method of claim 3, wherein amplicon is detected using a probe comprising:

```
                                              (SEQ ID NO: 3)
5' CACGCA-MeOG-C-MeOA-G-MeOA-C-MeOG-G-MeOG-MeOU-
G-MeOA-G-MeOU-A-MeOA-C-MeOG-TGCGTG 3'.
```

10. A method for detecting HLB in a plant or insect, the method comprising extracting a nucleic acid molecule from a plant or insect, contacting the extract with forward and reverse primers having the following sequences, respectively:

```
                                              (SEQ ID NO: 1)
5' GGACTCCATATGGAGTCCTCGCGAGCGG-MeOC-MeOA-MeOG-
MeOA-MeOC 3'
and (SEQ ID NO: 2)
5' TGACTCCATATGGAGTCATCTAGATTCC-MeOU-MeOA-MeOC-
MeOG-MeOC 3'
``` in the presence of a Nt.BstNBI(NEB) nicking enzyme, dNTPs, and a Bst DNA polymerase I for at least about ten minutes; and detecting the presence or absence of a *Liberibacter asiaticus* amplicon, wherein the presence of a *Liberibacter asiaticus* amplicon identifies an HLB infection in the plant or insect, and the absence of a *Liberibacter asiaticus* amplicon identifies the absence of an HLB infection in the plant or insect.

* * * * *

SEQUENCE LISTING

```
<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(33)
<223> OTHER INFORMATION: 2'-O-methyl nucleotide

<400> SEQUENCE: 1
ggactccata tggagtcctc gcgagcggca gac                               33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
```

```
                       primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (29)..(33)
<223> OTHER INFORMATION: 2'-O-methyl nucleotide

<400> SEQUENCE: 2
tgactccata tggagtcatc tagattccua cgc                                33

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<221> NAME/KEY: modified_base
<222> LOCATION: (7)..(7)
<223> OTHER INFORMATION: 2'-O-methyl nucleotide
<220> FEATURE:
<221> NAME/KEY: modified_base
<222> LOCATION: (9)..(9)
<223> OTHER INFORMATION: 2'-O-methyl nucleotide
<220> FEATURE:
<221> NAME/KEY: modified_base
<222> LOCATION: (11)..(11)
<223> OTHER INFORMATION: 2'-O-methyl nucleotide
<220> FEATURE:
<221> NAME/KEY: modified_base
<222> LOCATION: (13)..(13)
<223> OTHER INFORMATION: 2'-O-methyl nucleotide
<220> FEATURE:
<221> NAME/KEY: modified_base
<222> LOCATION: (15)..(16)
<223> OTHER INFORMATION: 2'-O-methyl nucleotide
<220> FEATURE:
<221> NAME/KEY: modified_base
<222> LOCATION: (18)..(18)
<223> OTHER INFORMATION: 2'-O-methyl nucleotide
<220> FEATURE:
<221> NAME/KEY: modified_base
<222> LOCATION: (20)..(20)
<223> OTHER INFORMATION: 2'-O-methyl nucleotide
<220> FEATURE:
<221> NAME/KEY: modified_base
<222> LOCATION: (22)..(22)
<223> OTHER INFORMATION: 2'-O-methyl nucleotide
<220> FEATURE:
<221> NAME/KEY: modified_base
<222> LOCATION: (24)..(24)
<223> OTHER INFORMATION: 2'-O-methyl nucleotide

<400> SEQUENCE: 3
cacgcagcag acgggugagu aacgtgcgtg                                    30
```